United States Patent
Namiki et al.

(10) Patent No.: US 11,051,897 B2
(45) Date of Patent: Jul. 6, 2021

(54) MEDICAL MANIPULATOR SYSTEM

(71) Applicant: OLYMPUS CORPORATION, Tokyo (JP)

(72) Inventors: Hirotaka Namiki, Tokorozawa (JP); Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 496 days.

(21) Appl. No.: 16/018,190

(22) Filed: Jun. 26, 2018

(65) Prior Publication Data

US 2018/0296290 A1    Oct. 18, 2018

Related U.S. Application Data

(63) Continuation of application No. PCT/JP2015/086539, filed on Dec. 28, 2015.

(51) Int. Cl.
*A61B 1/00*    (2006.01)
*A61B 34/30*   (2016.01)
(Continued)

(52) U.S. Cl.
CPC .......... *A61B 34/74* (2016.02); *A61B 1/00006* (2013.01); *A61B 1/00009* (2013.01); *A61B 1/00149* (2013.01); *A61B 34/10* (2016.02); *A61B 34/20* (2016.02); *A61B 34/30* (2016.02); *A61B 34/76* (2016.02); *A61B 90/361* (2016.02); *A61B 90/37* (2016.02); *B25J 9/1697* (2013.01); *A61B 1/0005* (2013.01); *A61B 34/25* (2016.02);
(Continued)

(58) Field of Classification Search
CPC combination set(s) only.
See application file for complete search history.

(56) References Cited

U.S. PATENT DOCUMENTS

2002/0103418 A1*  8/2002  Maeda ............... A61B 1/00149
                                                 600/132
2003/0055410 A1*  3/2003  Evans ................... A61B 34/32
                                                 606/1
(Continued)

FOREIGN PATENT DOCUMENTS

| JP | 2009-542362 A | 12/2009 |
| JP | 2015-150340 A | 8/2015 |
| WO | WO 2008/002830 A2 | 1/2008 |

OTHER PUBLICATIONS

International Search Report dated Feb. 9, 2016 issued in PCT/JP2015/086539.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A medical manipulator system includes: a first manipulator configured to change a position of an imaging section that images a target portion in a body; a second manipulator configured to change a position of an end effector that treats the target portion; a display section configured to display images from the imaging section; an operation section configured to generate an operation command for operating the first manipulator or the second manipulator; and a control section configured to select one of a plurality of control modes and control the first manipulator or the second manipulator based on the operation command.

15 Claims, 11 Drawing Sheets

(51) Int. Cl.
- *A61B 34/10* (2016.01)
- *A61B 34/00* (2016.01)
- *A61B 34/20* (2016.01)
- *A61B 90/00* (2016.01)
- *B25J 9/16* (2006.01)

(52) U.S. Cl.
CPC . *A61B 2034/107* (2016.02); *A61B 2034/2055* (2016.02); *A61B 2034/2059* (2016.02); *A61B 2034/301* (2016.02); *A61B 2090/365* (2016.02); *B25J 9/1692* (2013.01)

(56) References Cited

U.S. PATENT DOCUMENTS

| | | | |
|---|---|---|---|
| 2012/0158019 A1* | 6/2012 | Tenney | A61B 34/10 606/133 |
| 2013/0331644 A1* | 12/2013 | Pandya | A61B 1/00188 600/102 |
| 2014/0039681 A1* | 2/2014 | Bowling | B25J 13/00 700/261 |
| 2014/0046341 A1 | 2/2014 | DiCarlo | |
| 2014/0163359 A1* | 6/2014 | Sholev | A61B 1/04 600/424 |
| 2015/0313446 A1* | 11/2015 | Ogawa | A61B 1/0016 600/103 |
| 2016/0007827 A1* | 1/2016 | Frimer | A61B 17/00234 700/275 |
| 2016/0015473 A1* | 1/2016 | Frimer | A61B 1/00149 606/130 |
| 2016/0314710 A1* | 10/2016 | Jarc | G09B 23/285 |
| 2016/0339586 A1* | 11/2016 | Komuro | A61B 34/37 |
| 2017/0000574 A1* | 1/2017 | Itkowitz | A61B 34/37 |
| 2017/0172382 A1* | 6/2017 | Nir | A61B 1/00045 |

* cited by examiner

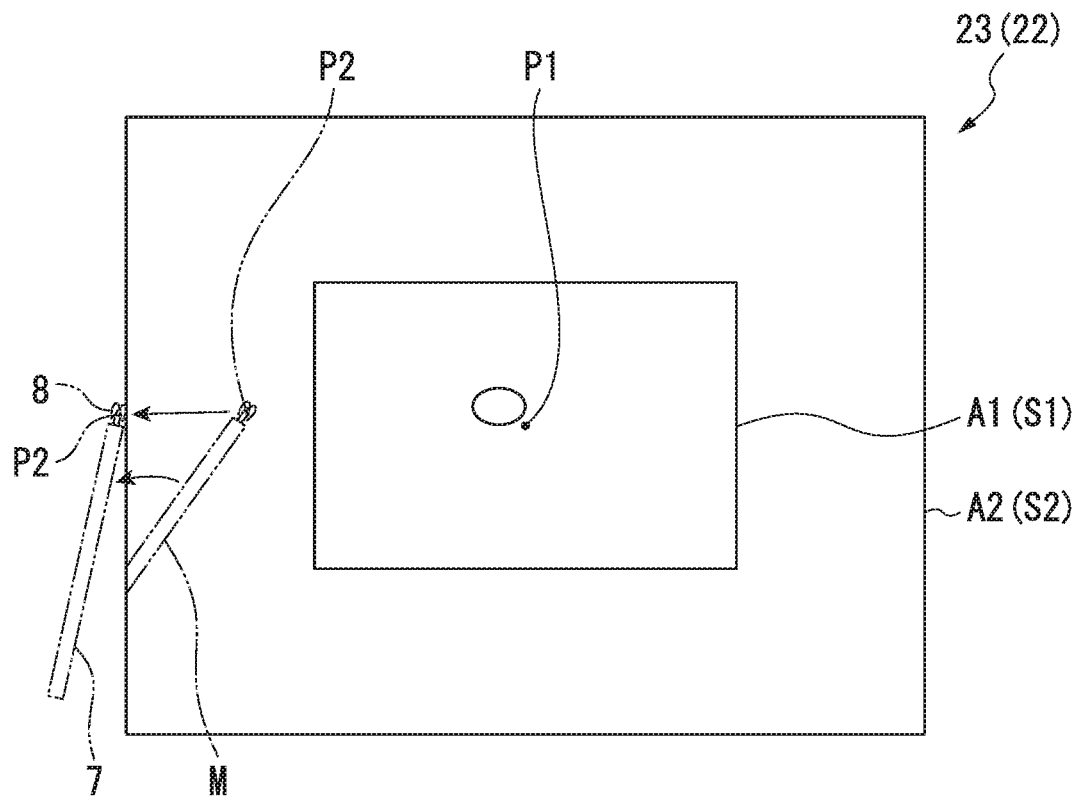

FIG. 12
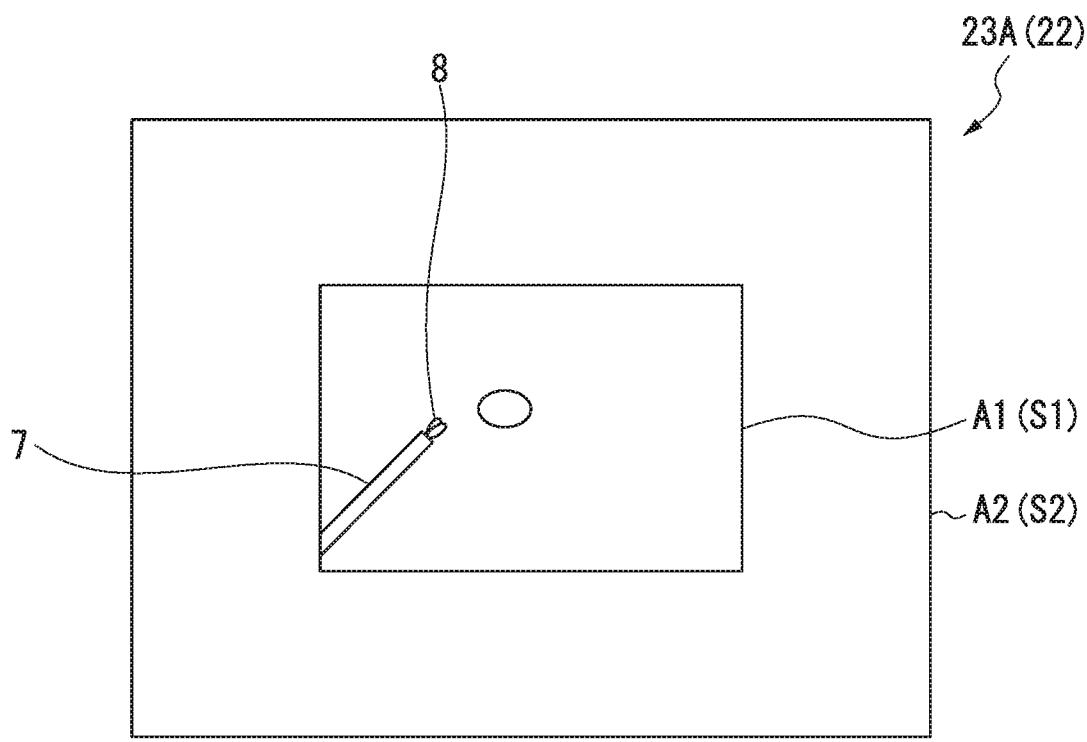
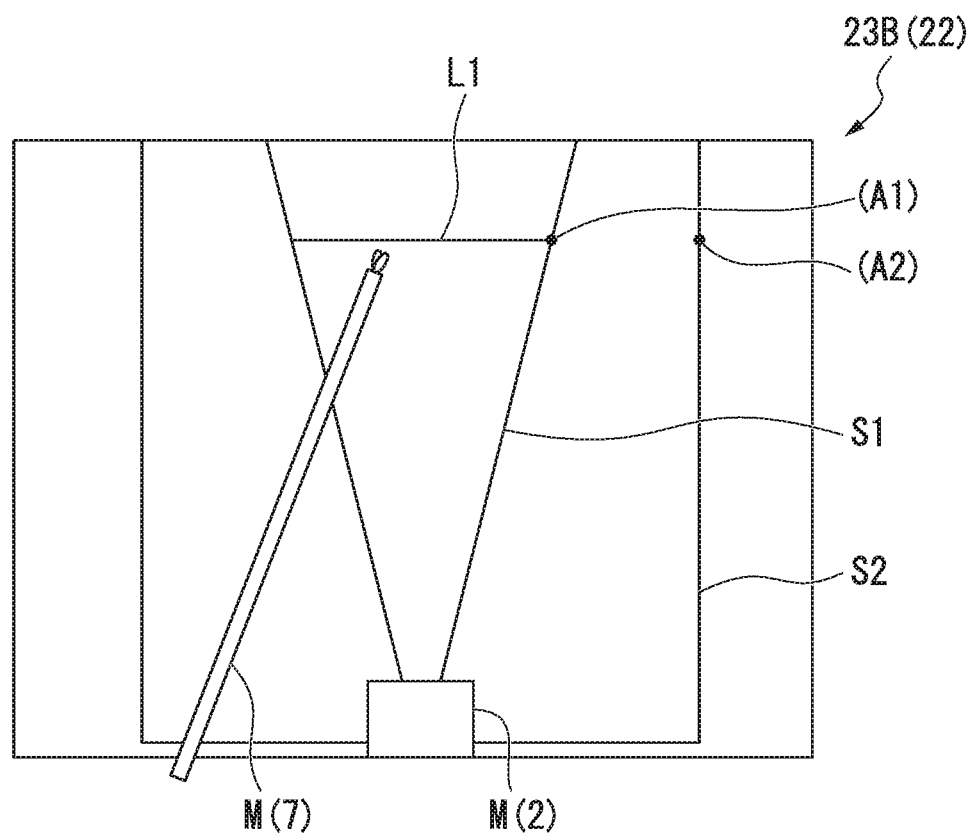

FIG. 15

|  |  | VIEW FIELD SPACE | |
|---|---|---|---|
|  |  | INSIDE | OUTSIDE |
| BOUNDARY SPACE | INSIDE | FIRST MODE | SECOND MODE |
| | OUTSIDE | FOURTH MODE | THIRD MODE |

MEDICAL MANIPULATOR SYSTEM

CROSS REFERENCE TO RELATED APPLICATIONS

This application is a continuation application based on a PCT Patent Application No. PCT/JP2015/086539, filed on Dec. 28, 2015, the entire content of which is hereby incorporated by reference.

BACKGROUND

Technical Field

The present invention relates to a medical manipulator system.

Background Art

Conventionally, a medical manipulator system is known which performs surgery using a treatment instrument with respect to a treatment target portion while observing the portion with an endoscope. For example, Published Japanese Translation No. 2009-542362 of the PCT International Publication discloses a technique for displaying the position and orientation of a treatment tool located outside the view field of the endoscope in a boundary area set outside the display area of the endoscopic image.

According to the technique disclosed in Published Japanese Translation No. 2009-542362 of the PCT International Publication, the operator can easily grasp the position and orientation of the treatment instrument located outside the field of view of the endoscope, and the treatment instrument outside the field of view of the endoscope can be easily moved to the field of view.

SUMMARY

A medical manipulator system includes: a first manipulator configured to change a position of an imaging section that images a target portion in a body; a second manipulator configured to change a position of an end effector that treats the target portion; a display section configured to display images from the imaging section; an operation section configured to generate an operation command for operating the first manipulator or the second manipulator; and a control section configured to select one of a plurality of control modes and control the first manipulator or the second manipulator based on the operation command. The control section includes: a view field area acquisition section configured to acquire an image of a predetermined portion imaged by the imaging section to acquire a view field area; an position information acquisition section configured to acquire a first position that is a position at center of the view field area, and to acquire a second position that is a position of a tip of the end effector within the view field area or outside the view field area as long as the second manipulator can move while imaging the predetermined portion; and a determination section configured to select one mode from the plurality of control modes based on the view field area, the first position, and the second position. The plurality of control modes include: a first mode in which operation of the second manipulator by the operation section is fully permitted; a second mode in which a predetermined restriction is imposed on the operation command by the operation section and operation of the second manipulator is permitted within the restriction; and a third mode in which operation of the second manipulator by the operation section is inhibited. The determination section is configured to select the first mode when the second position is within the view field area, select the second mode when the second position is outside the view field area and a distance between the first position and the second position is equal to or less than a predetermined value, and select the third mode when the second position is outside the view field area and the distance between the first position and the second position is more than the predetermined value.

The display section may include: a view field display section configured to display the image imaged by the imaging section; and an auxiliary display section configured to display an index corresponding to presence of the second manipulator.

In the second mode, operating speed of the second manipulator may be restricted so that the second manipulator is operated with lower speed than operating speed of the second manipulator in the first mode.

In the second mode, operable direction of the second manipulator may be restricted compared with the first mode.

In the second mode, the operable direction may be restricted only to a direction in which the second position directs toward the view field area.

The medical manipulator system may further include a setting means configured to set contents of the restriction in the second mode.

The second manipulator may further include a contact detection means configured to detect that the second manipulator has touched an object, and in the second mode, when the contact detection means detects that the second manipulator and the object are in contact with each other, an operator may be notified that the second manipulator and the object have come into contact with each other and control mode may shift to the third mode.

A control apparatus of a medical manipulator system, includes a control section configured to control a first manipulator having an imaging section configured to image a target portion in a body and a second manipulator configured to treat the target portion in the body, based on operation command by selecting one mode from a plurality of control modes. The control section includes: a view field area acquisition section configured to acquire an image of a predetermined portion imaged by the imaging section to acquire a view field area; an position information acquisition section configured to acquire a first position that is a position at center of the view field area, and to acquire a second position that is a position of a tip of the end effector within the view field area or outside the view field area as long as the second manipulator can move while imaging the predetermined portion; and a determination section configured to select one mode from the plurality of control modes based on the view field area, the first position, and the second position. The plurality of control modes include: a first mode in which operation of the second manipulator by the operation section is fully permitted; a second mode in which a predetermined restriction is imposed on the operation command by the operation section and operation of the second manipulator is permitted within the restriction; and a third mode in which operation of the second manipulator by the operation section is inhibited. The determination section is configured to select the first mode when the second position is within the view field area, select the second mode when the second position is outside the view field area and a distance between the first position and the second position is equal to or less than a predetermined value, and select the third mode when the second position is outside the view field area and the distance between the first position and the second position is more than the predetermined value.

A method of controlling a medical manipulator system, wherein the medical manipulator system includes a first manipulator having an imaging section, a second manipulator having an end effector, and a display section for displaying an image from the imaging section, includes: acquiring, by a view field area acquisition section, an image imaged by the imaging section to acquire a view field area; acquiring, by an position information acquisition section, a first position that is a position at center of the view field area and a second position that is a position of a tip of the second manipulator; selecting, by a determination section, one mode from a plurality of control modes based on the view field area, the first position, and the second position, the plurality of control modes including a first mode in which operation of the second manipulator by the operation section is fully permitted, a second mode in which a predetermined restriction is imposed on the operation command by the operation section and operation of the second manipulator is permitted within the restriction, and a third mode in which operation of the second manipulator by the operation section is inhibited; selecting, by the determination section, the first mode when the second position is within the view field area, the second mode when the second position is outside the view field area and a distance between the first position and the second position is equal to or less than a predetermined value, or the third mode when the second position is outside the view field area and the distance between the first position and the second position is more than the predetermined value.

The method of controlling a medical manipulator system may further include: displaying, by a view field display section, the image imaged by the imaging section; and displaying, by an auxiliary display section, an index corresponding to presence of the second manipulator.

The method of controlling a medical manipulator system may further include: restricting, in the second mode, operating speed of the second manipulator so that the second manipulator is operated with lower speed than operating speed of the second manipulator in the first mode.

The method of controlling a medical manipulator system may further include: restricting, in the second mode, operable direction of the second manipulator compared with the first mode.

The method of controlling a medical manipulator system may further include: restricting, in the second mode, the operable direction only to a direction in which the second position directs toward the view field area.

The method of controlling a medical manipulator system may further include: setting, by a setting means, contents of the restriction in the second mode.

The method of controlling a medical manipulator system may further include: detecting, by a contact detection means, that the second manipulator has touched an object; and when the contact detection means detects that the second manipulator and the object are in contact with each other in the second mode, notifying an operator that the second manipulator and the object have come into contact with each other and prohibiting operation of the second manipulator by the operation section.

BRIEF DESCRIPTION OF THE DRAWINGS

FIG. 7 is a schematic diagram showing an image displayed on a display section of the medical manipulator system of the present embodiment.

FIG. 8 is a table showing conditions for selecting one mode from a plurality of control modes.

FIG. 12 is a schematic diagram showing an example of an image displayed on a display section of the medical manipulator system of the modified example.

FIG. 15 is a table showing conditions for selecting one mode from a plurality of control modes.

DETAILED DESCRIPTION OF THE PREFERRED EMBODIMENTS

Figure 1:
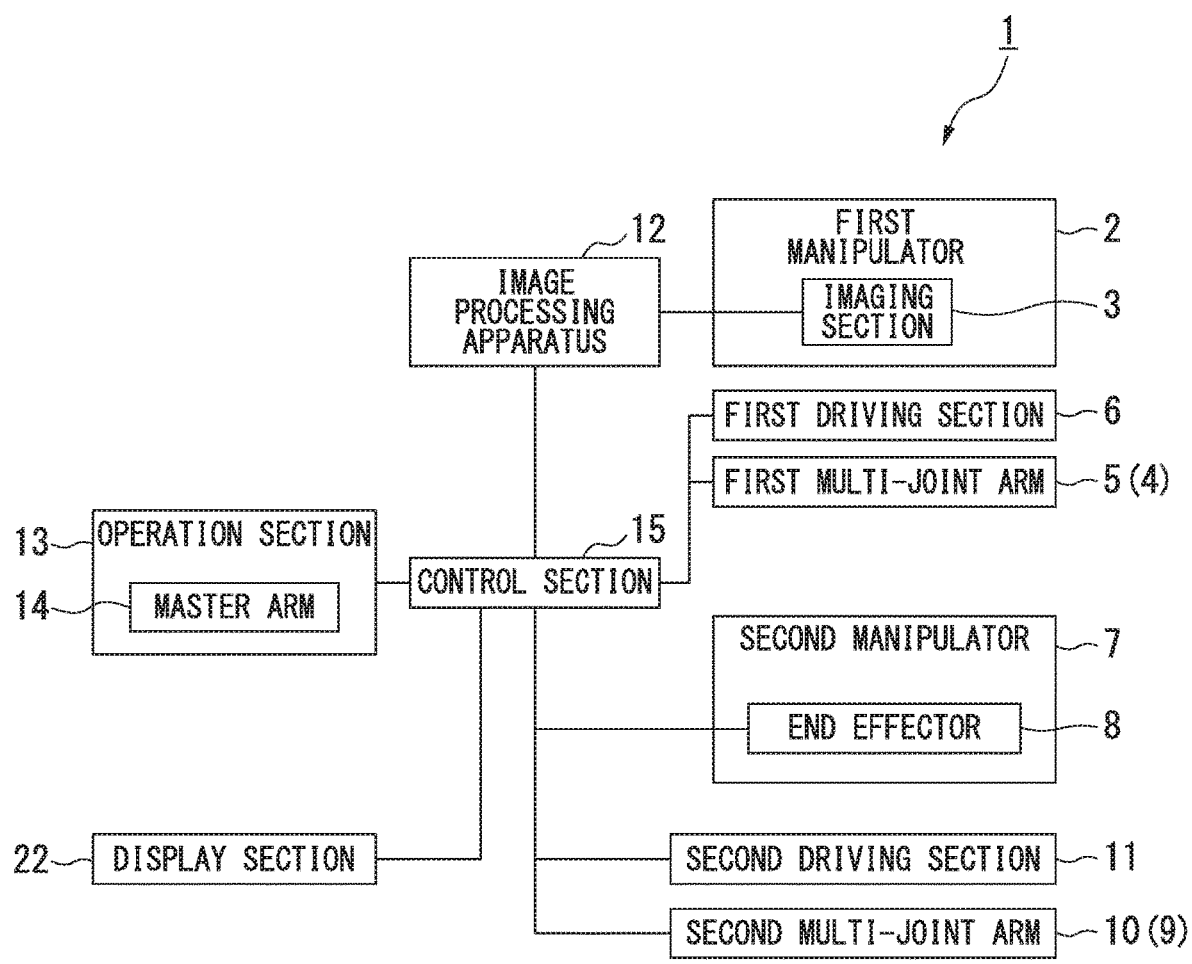
FIG. 1 is a block diagram of a medical manipulator system according to an embodiment of the present invention.

One embodiment of the present invention will be described. FIG. 1 is a block diagram of a medical manipulator system of the present embodiment.

As shown in FIG. 1, the medical manipulator system 1 of the present embodiment includes: a first manipulator 2 having an imaging section 3; a first position/orientation detection section 4 for detecting the position and orientation of the first manipulator 2 in a predetermined reference coordinate system; a first driving section 6 for driving the first manipulator 2; a second manipulator 7 having an end effector 8; a second position/orientation detection section 9 for detecting the position and orientation of the second manipulator 7 in the predetermined reference coordinate system; a second driving section 11 for driving the second manipulator 7; an image processing apparatus 12 connected to the imaging section 3 of the first manipulator 2; a operation section 13 for operating the first manipulator 2 and the second manipulator 7; a control section 15 for controlling the first manipulator 2 and the second manipulator 7 based on an operation input to the operation section 13; and a display section 22 connected to the control section 15.

The first manipulator 2 is a manipulator for observing a treatment target portion in the body using the imaging section 3. The imaging section 3 of the first manipulator 2 is electrically connected to the image processing apparatus 12 so as to capture an image of the imaging target and transmit the electric signal to the image processing apparatus 12.

The first position/orientation detection section 4 has a first multi-joint arm 5 that holds the first manipulator 2. The first multi-joint arm 5 includes an encoder (not shown) for detecting the position and orientation of the first manipulator 2. The encoder provided on the first multi-joint arm 5 is connected to the control section 15.

The first driving section 6 has an actuator (not shown) for moving the imaging section 3 of the first manipulator 2. In the present embodiment, the actuator of the first driving section 6 is disposed at each joint of the first multi-joint arm 5. The first driving section 6 drives the first multi-joint arm 5 by the actuator in accordance with a control signal from the control section 15, thereby driving the first manipulator 2.

Here, another actuator (not shown) for changing the direction of view field of the imaging section 3 of the first manipulator 2 may be arranged in the first manipulator 2, and in this case, this actuator is controlled by the control section 15 as a part of the first driving section 6.

The second manipulator 7 is a manipulator for surgically treating the treatment target portion in the body using the end effector 8.

The end effector 8 of the second manipulator 7 is connected to the second driving section 11 so as to be driven by the second driving section 11. For example, the end effector 8 of the present embodiment is a forceps or a pair of scissors which is opened and closed by the second driving section 11. Here, the end effector 8 need not be mechanically driven. For example, the end effector 8 may be an electric scalpel, an ultrasonic knife, or the like.

The second position/orientation detection section 9 has a second multi-joint arm 10 that holds the second manipulator 7. The second multi-joint arm 10 includes an encoder (not shown) for detecting the position and orientation of the second manipulator 7. An encoder provided in the second multi-joint arm 10 is connected to the control section 15.

When the end effector 8 can perform an operation such as swinging motion in the second manipulator 7, the encoder of the second position/orientation detection section 9 may include a first encoder for detecting the position and orientation of the second manipulator 7 itself and a second encoder for detecting the position and orientation of the end effector 8.

The second driving section 11 has an actuator (not shown) for moving the entire second manipulator 7 and an actuator (not shown) for driving the end effector 8 of the second manipulator 7. In the present embodiment, the actuator for moving the entire second manipulator 7 is disposed at each joint of the second multi-joint arm 10. In the present embodiment, the actuator for driving the end effector 8 is disposed at the distal end of the second multi-joint arm 10. The second driving section 11 drives the second manipulator 7 by driving the end effector 8 and the second multi-joint arm 10 by each actuator according to a control signal from the control section 15.

The image processing apparatus 12 receives the electric signal transmitted from the imaging section 3 and converts the electric signal into an image signal. The image processing apparatus 12 outputs the image signal to the control section 15. Here, the image processing apparatus 12 may include outputs of plural systems so that the image signal can be output to the display section 22 in addition to the control section 15.

The operation section 13 is an input device used by an operator who operates the first manipulator 2 and the second manipulator 7. The operation section 13 generates an operation command corresponding to the input by the operator. The operation command generated by the operation section 13 is output to the control section 15. For example, the operation section 13 of the present embodiment for operating the second manipulator 7 has a master arm 14 similar to a distal portion of the second manipulator 7 and the end effector 8. By moving the master arm 14 by the operator, the entire second manipulator 7 can be moved. The operator operates a portion of the master arm 14 corresponding to the end effector 8, so that the end effector 8 can be operated. In addition, the master arm 14 has resistance means (not shown) for changing the amount of force required for the operator to operate the master arm 14.

Figure 2:
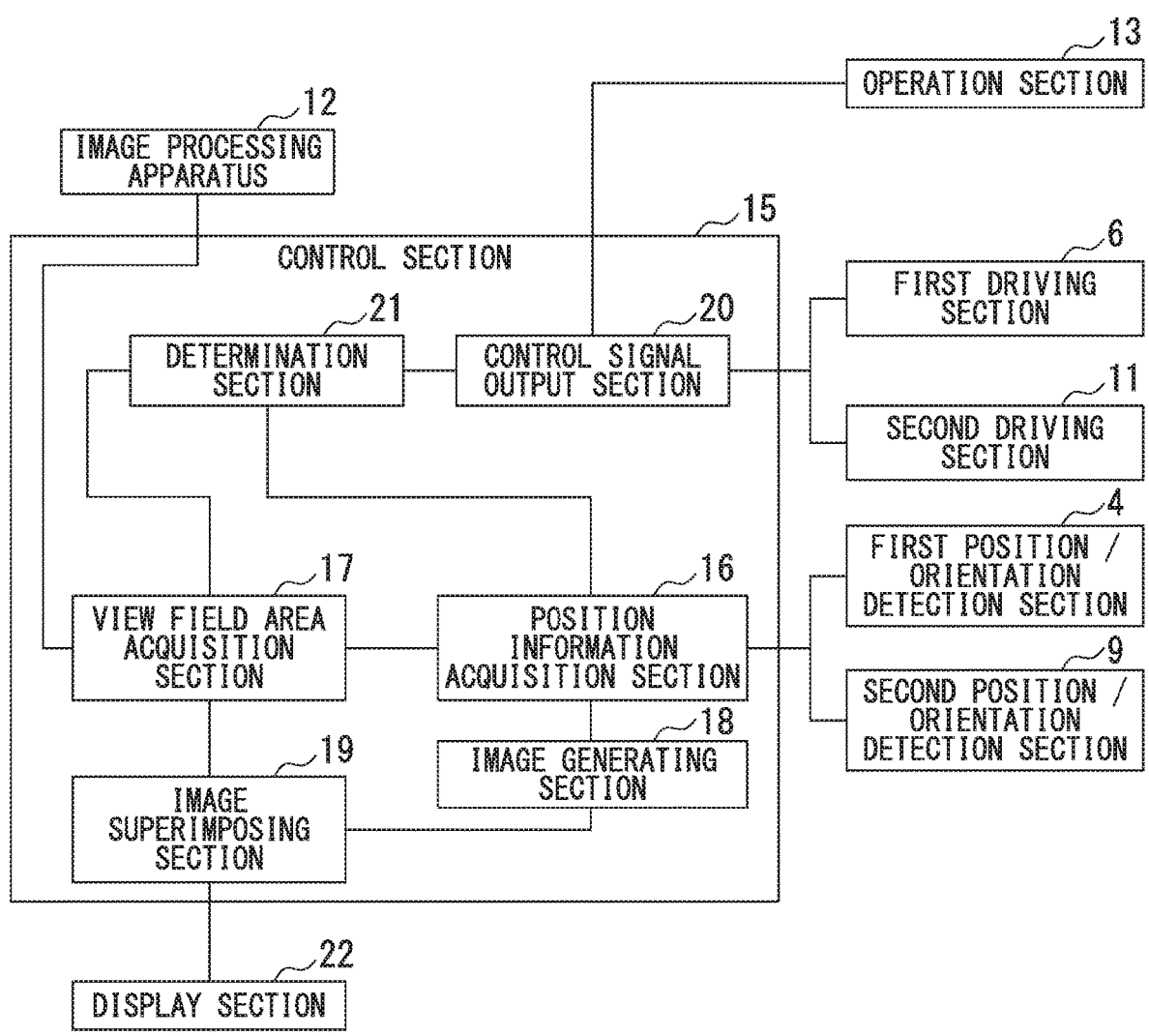
FIG. 2 is a block diagram showing a part of a medical manipulator system according to the present embodiment.
Figure 3:
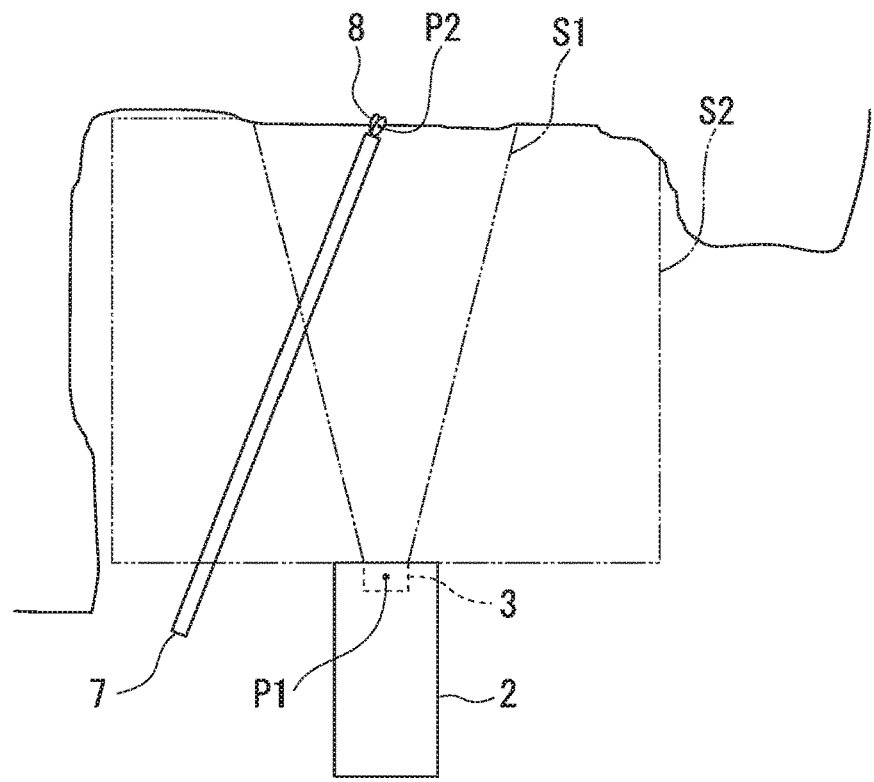
FIG. 3 is a schematic diagram showing a view field space and a boundary space defined by the medical manipulator system of the present embodiment.
Figure 4:
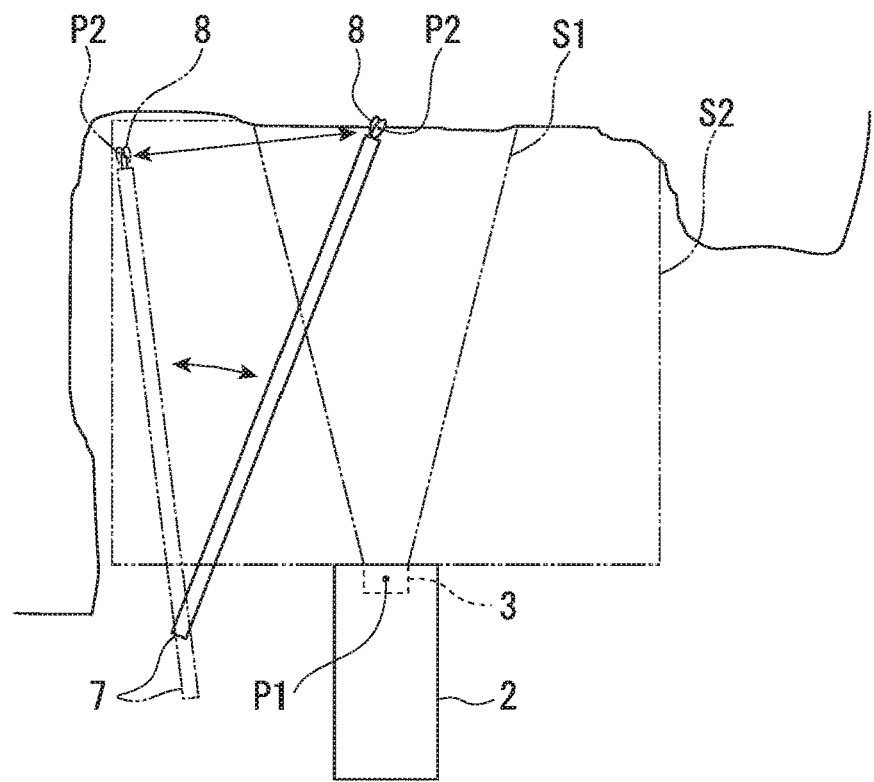
FIG. 4 is a schematic diagram showing a view field space and a boundary space defined by the medical manipulator system of the present embodiment.
Figure 5:
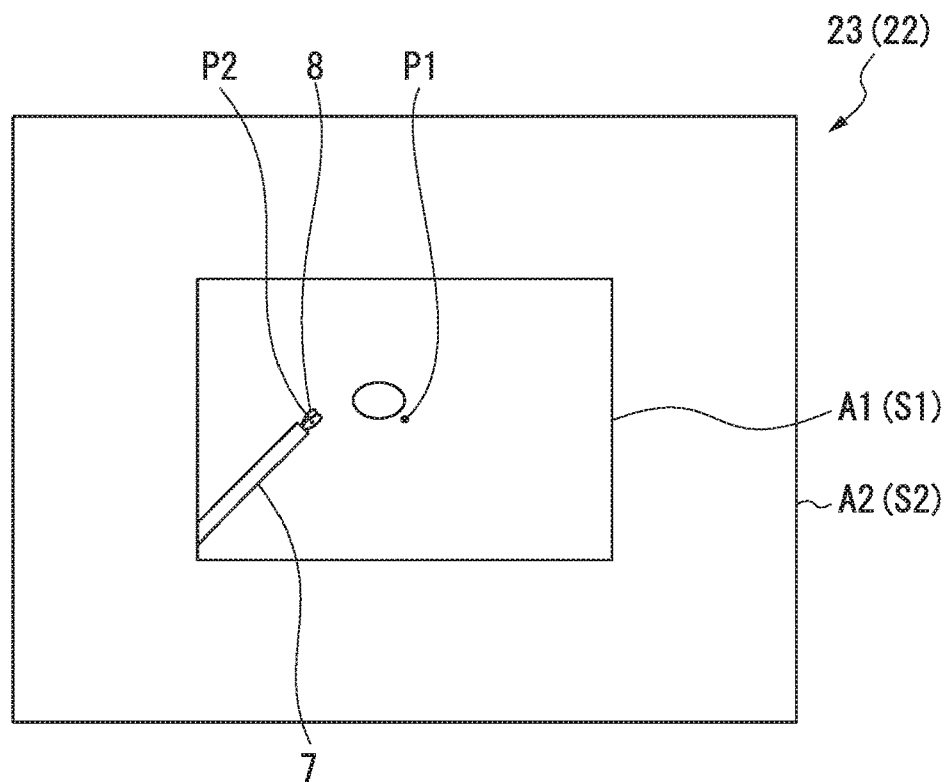
FIG. 5 is a schematic diagram showing an image displayed on a display section of the medical manipulator system of the present embodiment.
Figure 6:
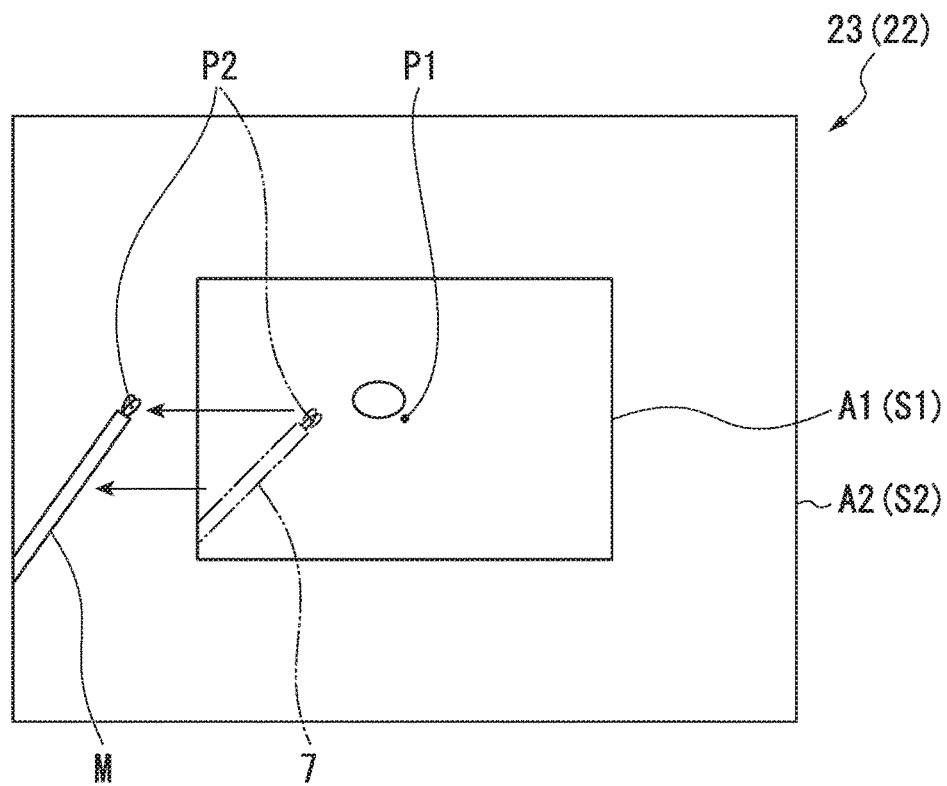
FIG. 6 is a schematic diagram showing an image displayed on a display section of the medical manipulator system of the present embodiment.

FIG. 2 is a block diagram showing a part of the medical manipulator system of the present embodiment. FIGS. 3 and 4 are schematic diagrams showing a view field space and a boundary space defined by the medical manipulator system of the present embodiment. FIGS. 5, 6, and 7 are schematic views showing images displayed on the display section of the medical manipulator system of the present embodiment.

As shown in FIG. 1, in order to control the first manipulator 2 and the second manipulator 7, the control section 15 is electrically connected to the first manipulator 2, the first position/orientation detection section 4, the first driving section 6, the second manipulator 7, the second position/orientation detection section 9, the second driving section 11, the image processing apparatus 12, and the operation section 13.

As shown in FIG. 2, the control section 15 includes a position information acquisition section 16, a view field area acquisition section 17, an image generating section 18, an image superimposing section 19, a control signal output section 20, and a determination section 21.

The position information acquisition section 16 refers to the encoder provided in the first position/orientation detection section 4 and acquires information on the position and orientation of the first manipulator 2. Further, the position information acquisition section 16 refers to the encoder provided in the second position/orientation detection section 9 and acquires the position and orientation of the second manipulator 7. In the present embodiment, the position information acquisition section 16 acquires the portion of the imaging section 3 of the first manipulator 2 in the reference coordinate system as the first position P1 (see FIGS. 3 and 4) and acquires the portion of the end effector 8 of the second manipulator 7 in the reference coordinate system as the second position P2 (see FIGS. 3 and 4).

The reference coordinate system in the present embodiment is an orthogonal coordinate system in which the predetermined position set for the medical manipulator of the present embodiment is defined as the origin.

The information on the first position P1 includes the coordinates of the position of the imaging section 3 and the information on the orientation thereof, and the information on the second position P2 includes the coordinates of the position of the end effector 8 and information on the orientation thereof.

The view field area acquisition section 17 receives the image signal output from the image processing apparatus 12. That is, the view field area acquisition section 17 acquires the image taken by the imaging section 3 via the image processing apparatus 12.

Further, the view field area acquisition section 17 defines the view field space 51 within the body space in which the imaging section 3 is disposed (see FIGS. 3 and 4), based on the optical characteristics such as the angle of view of the imaging section 3 and the position and orientation of the imaging section 3 (information on the first position P1). For example, the view field area acquisition section 17 calculates the position of the view field space S1 in the reference coordinate system based on the optical characteristics such as the angle of view of the imaging section 3 and the position and orientation of the imaging section 3 (information on the first position P1). The view field space S1 may be a part including the center of the field of view of the range that can be imaged by the imaging section 3, or may be a space defined by the angle of view of the imaging section 3.

The view field space S1 corresponds to the imaging view field of the imaging section 3 (view field area A1, see FIG. 5) in the image displayed on the display section 22.

The view field area acquisition section 17 defines a boundary space S2 (see FIGS. 3 and 4) around the view field space S1. For example, the outer boundary of the boundary space S2 is set based on the movable range of the second manipulator 7. Further, the outer boundary of the boundary space S2 may be set, for example, based on the shape of a space in which the second manipulator 7 can move at the site in the body where the second manipulator 7 is disposed. The setting of the outer boundary of the boundary space S2 based on the shape of the space in which the second manipulator 7 can move within the body may be performed based on the measurement result of the shape of the space or may be performed based on a rough outline as a standard shape of internal organs in the body where the second manipulator 7 is disposed.

The boundary space S2 corresponds to an area (boundary area A2, see FIG. 5) outside the imaging field of view located around the view field area A1 in the image displayed on the display section 22.

The image generating section 18 generates an image showing the state of the second manipulator 7 viewed from the direction of view field of the imaging section 3 by computer graphics (see FIG. 6). For example, based on the position and orientation of the imaging section 3 in the reference coordinate system and the position and orientation of the second manipulator 7 in the reference coordinate system, the image generating section 18 calculates the drawing position of the second manipulator 7 on the image and the orientation of the second manipulator 7 to generate an image including an index M that imitates the shape of the second manipulator 7. The image generated by the image generating section 18 includes an index M having a shape corresponding to at least the end effector 8 of the second manipulator 7.

In the present embodiment, when the end effector 8 is located outside the view field space S1 and within the boundary space S2, the image generating section 18 generates an image including the index M, and when the end effector 8 is located within the view field space S1, the image generating section 18 generates an image not including the index M.

The image generating section 18 may generate a stereoscopic image including the index M imitating the shape of the end effector 8 (for example, a set of images configured by considering the parallax so as to correspond to the left eye and the right eye of the operator).

The image generating section 18 may generate an image including a background in addition to the index M. The background in the image generated by the image generating section 18 may be, for example, an image obtained by image diagnosis performed in advance on a patient to be treated using the medical manipulator system 1 of the present embodiment (for example, a CT image, an MRI image, or the like), an image reconstructed based on past images imaged by the imaging section 3 of the first manipulator 2, or the like.

The image superimposing section 19 outputs a superimposed image formed by integrating the image signal output by the image processing apparatus 12 to the control section 15 and the image generated by the image generating section 18 to the display section 22. The image superimposing section 19 sets a part of the entire displayable area of the display section 22 as a display area of the image (view field area A1 on display) imaged by the imaging section 3. Further, the image superimposing section 19 sets the area other than the view field area A1 in the displayable area of the display section 22 as a display area of the image (boundary area A2 on display) generated by the image generating section 18. For example, the image superimposing section 19 of the present embodiment superimposes an image from the image processing apparatus 12 on the image generated by the image generating section 18 so that the image from the image processing apparatus 12 is positioned at the center of the image generated by the image generating section 18, to output to the display section 22. As a result, as shown in FIG. 5, the central portion of the displayable area of the display section 22 becomes the view field area A1, and the outside of the view field area A1 becomes the boundary area A2.

As shown in FIG. 2, the control signal output section 20 generates a control signal for operating the first manipulator 2 according to an operation input to the operation section 13, and outputs the control signal to the first driving section 6.

In addition, the control signal output section 20 generates a control signal for operating the second manipulator 7 according to an operation input to the operation section 13, and outputs the control signal to the second driving section 11. Further, the control signal output section 20 outputs, to the operation section 13, a control signal for changing the limitation on the operation command by the operation section 13 according to one mode selected by the determination section 21 among the plurality of control modes.

The plurality of control modes include a first mode in which operation of the second manipulator 7 by the operation section 13 is permitted, a second mode in which operation of the second manipulator 7 is permitted within the limitation by adding a predetermined limitation to the operation command by the operation section 13, and a third mode in which the operation of the second manipulator 7 by the operation section 13 is prohibited.

In the first mode, the resistance means does not function as a resistor, and the operator can freely manipulate the master arm 14.

The predetermined limitation in the second mode is a limitation for improving the usability more than the first mode with respect to the operation of the second manipulator 7. The predetermined limitation in the second mode of the present embodiment is a limitation such that the moving speed of the second manipulator 7 is lower than the moving speed of the second manipulator 7 in the first mode. For example, when the second mode is selected, the resistance means increases the resistance with respect to the input of operation on the master arm 14 of the operation section 13, thereby lowering the speed of input to the master arm 14. As a result, the moving speed of the second manipulator 7 is lowered.

The prohibition of the operation in the third mode is a control in which the resistance means increases the resistance so that the master arm 14 of the operation section 13 becomes inoperable.

Based on a plurality of conditions corresponding to the positional relationship between the position of the imaging section 3 (first position P1) and the position of the end effector 8 (second position P2) in the space where the imaging section 3 is located, one mode is selected from the first mode, the second mode, and the third mode.

FIG. 8 is a table showing conditions for selecting one mode from a plurality of control modes.

When the second position P2 is within the view field space S1 (when the second position P2 is within the view field area A1 on display of the display section 22) (see FIG. 5), the determination section 21 of the present embodiment selects the first mode.

Further, when the second position P2 is located outside the view field space S1 (the second position P2 is located outside the view field area A1 on display of the display section 22) and the distance between the first position P1 and the second position P2 (the distance measured along the plane orthogonal to the direction of view field of the imaging section 3) is equal to or less than the predetermined value (see FIG. 6), the determination section 21 of the present embodiment selects the second mode.

Further, when the second position P2 is located outside the view field space S1 (the second position P2 is located outside the view field area A1 on display of the display section 22) and the distance between the first position P1 and the second position P2 (the distance measured along the plane orthogonal to the direction of view field of the imaging section 3) exceeds the predetermined value (see FIG. 7), the determination section 21 of the present embodiment selects the third mode.

The predetermined value concerning the distance between the first position P1 and the second position P2 is, for example, a distance from the center of the field of view of the imaging section 3 in a plane orthogonal to the direction of view field of the imaging section 3 and including the second position P2 to the outer boundary of the boundary area A2. The predetermined value is not limited to a constant value. For example, in the case where the boundary area A2 is circular (in the case where the outer boundary of the boundary space S2 is a columnar shape or a conical shape), the predetermined value is a constant value. Further, for example, when the boundary area A2 is other than a circle, the predetermined value is a distance between the outer boundary of the boundary area A2 and the center of the field of view, and varies depending on the site.

In the present embodiment, the outer boundary of the boundary space S2 is determined in advance or based on the measurement result of the internal tissue, corresponding to the shape of the tissue. Therefore, in the present embodiment, it can be regarded that the end effector 8 is hard to come into contact with the tissue or the like inside the body even if the end effector 8 is moved in the space inside the outer boundary of the boundary space S2.

The display section 22 displays the superimposed image constituted by the image superimposing section 19 of the control section 15. The display section 22 has a display panel 23 capable of displaying a superimposed image. In a state in which a superimposed image is displayed on the display panel 23, the display panel 23 can be classified into a view field display section 22a which is a part for displaying the image imaged by the imaging section 3, and an auxiliary display section 22b which is a part capable of displaying an index M corresponding to the presence of the second manipulator 7.

The display section 22 may have a plurality of input systems and selectors so that either one of the image output from the control section 15 and the image output from the image processing apparatus 12 can be displayed selectively.

The operation of the medical manipulator system 1 of the present embodiment will be described.

When using the medical manipulator system 1 of the present embodiment, in the medical manipulator system 1, the determination section 21 switches the control mode based on the positional relationship between the imaging section 3 and the end effector 8.

When the end effector 8 is within the view field area A1 (see FIG. 5), the determination section 21 selects the first mode from a plurality of control modes, so that the end effector 8 can freely move according to the operation in the operation section 13.

When the end effector 8 is outside the view field area A1 and within the boundary area A2 (see FIG. 6), the determination section 21 selects the second mode from a plurality of control modes, so that the end effector 8 can freely move while the moving speed of the end effector 8 is limited.

When the end effector 8 is outside the boundary area A2 (see FIG. 7), the determination section 21 selects the third mode from a plurality of control modes, so that the end effector 8 stops without reacting to the operation by the operation section 13.

In any of the first mode, the second mode, and the third mode, it is possible to operate the first manipulator 2 using the operation section 13. Therefore, when the state is shifted from the state controlled in the first mode or the second mode to the third mode and the end effector 8 is stopped, if the operator operates the first manipulator 2 to return to the state where the second manipulator 7 is positioned in the view field space S1 or the boundary space S2, the mode is shifted from the third mode to the first mode or the second mode and the operation of the second manipulator 7 and the end effector 8 can be resumed. The manner of returning may be operated via the operation section 13 or may be changed directly by hand with the position of the first manipulator 2 or the like.

The second manipulator 7 is not included in the image from the imaging section 3 in a state in which the second manipulator 7 is located outside the view field space S1 and within the boundary space S2. For example, in a state in which the end effector 8 is located outside the view field space S1 and within the boundary space S2, the end effector 8 is not displayed in the view field area A1 but is displayed in the boundary area A2 as an index M by computer graphics.

In the medical manipulator system 1 of the present embodiment, even if the end effector 8 of the second manipulator 7 is located outside the view field space S1, when the end effector 8 is positioned within the boundary space S2, the second manipulator 7 can be operated within the predetermined limit (second mode). When the end effector 8 is located outside the view field space S1 and within the boundary space S2, an index M indicating the end effector 8 is displayed in the boundary area A2 in the superimposed image displayed on the display section 22. Therefore, even if the end effector 8 is not imaged by the imaging section 3, it is easy to grasp the position and orientation of the end effector 8. As a result, in the medical manipulator system 1 of the present embodiment, even if there is the second manipulator 7 outside the field of view of the imaging section 3, the second manipulator 7 can be operated freely within the range of the above limitation, and the usability is good.

In addition, since the movement of the end effector 8 is stopped when the end effector 8 moves to the outside of the boundary space S2, the possibility of the end effector 8 being inadvertently brought into contact with tissues or the like in the body can be suppressed to be low.

(Modification 1)

Modifications of the above embodiment will be described. In each of the following modifications, the same reference numerals as in the above embodiment denote the same constituent elements as those disclosed in the above embodiment, and redundant explanations are omitted.

In the medical manipulator system 1 of the present modification (see FIG. 1), the second manipulator 7 is controlled so that the movable speed of the second manipulator 7 gradually decreases as the second manipulator 7 approaches the outer boundary in the boundary space S2, which is different from the above embodiment.

As an example, in the present modification, the control section 15 controls the resistance means so that the resistance by the resistance means of the master arm 14 gradually increases as the end effector 8 approaches the outer boundary of the boundary space S2. As a result, it becomes gradually difficult to move the master arm 14 as the end effector 8 approaches the boundary space S2. Conversely, as the end effector 8 moves away from the boundary space S2 toward the view field space S1, the control section 15 controls the resistance means so as to gradually make the resistance by the resistance means smaller. As a result, as the end effector 8 moves away from the boundary space S2 toward the view field space S1, the difficulty in moving the master arm 14 is gradually eliminated.

In the present modification, the moving speed of the second manipulator 7 at the time of shifting from the first mode to the second mode is substantially equal to the moving speed in the first mode, and just before the transition from the second mode to the third mode, the moving speed of the second manipulator 7 is in a substantially stopped state. Therefore, in the present modification, the change in the moving speed of the second manipulator 7 when entering the boundary area A2 from out of the view field area A1 is smooth, which is convenient.

(Modification 2)

Figure 9:
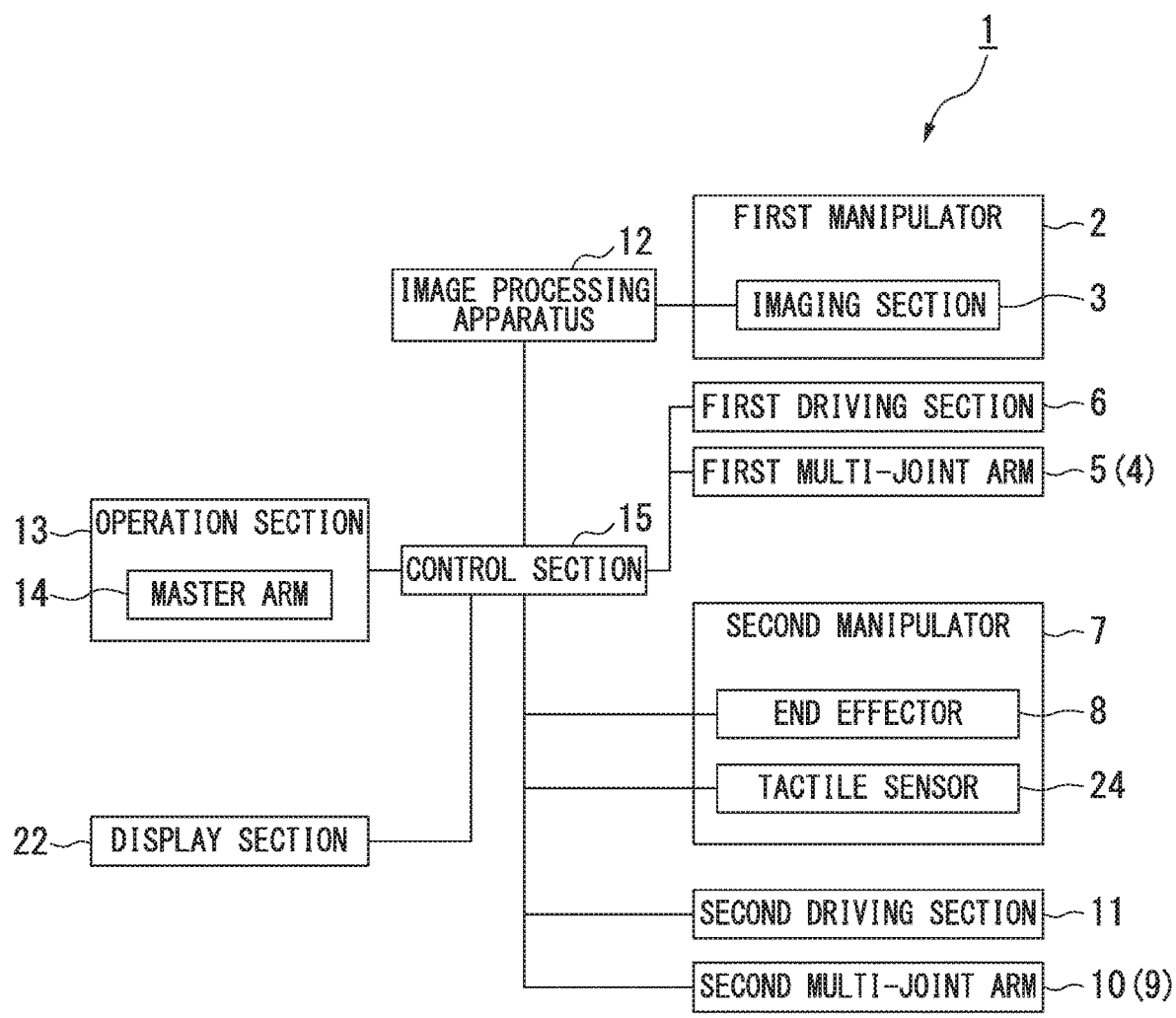
FIG. 9 is a block diagram of a medical manipulator system according to a modification of the present embodiment.

Another modification of the above embodiment will be described. FIG. 9 is a block diagram of the medical manipulator system of the present modification.

As shown in FIG. 9, in the medical manipulator system 1 of the present modification, the second manipulator 7 includes a tactile sensor 24 (contact detection means) that detects the amount of force by which the object pushes back the second manipulator 7 as the second manipulator 7 contacts the object, and the master arm 14 has feedback means (not shown) for transmitting the force detected by the sensor of the second manipulator 7 to the operator's hand.

In the medical manipulator system 1 of the present modification, in the first mode, the feedback means operates with a predetermined correspondence relationship with the force detected by the tactile sensor 24. For example, in response to the elasticity when the second manipulator 7 touches the tissue inside the body, the feedback means transmits the amount of force from the master arm 14 to the operator so that the operator who operates the master arm 14 feels the same degree of elasticity as if directly touching this tissue.

Further, in the second mode, the medical manipulator system 1 of the present modification conveys a greater amount of force than the force sensed by the operator in the first mode to the operator from the master arm 14 in response to the force sensed by the tactile sensor 24.

In the present modification, in the second mode, the operator can grasp that the end effector 8 is located outside the view field space S1 and in the boundary space S2 by using the display section 22. However, since the end effector 8 is not displayed on the image imaged by the imaging section 3, the second manipulator 7 is operated by intuition depending on the tactile sense for the sake of caution. In the second mode, it is easier to perceive that the second manipulator 7 has touched the object than in the first mode, so that it is convenient to move the second manipulator 7 in the boundary space S2.

In the present modification, when the tactile sensor 24 detects the contact between the second manipulator 7 and the object while the medical manipulator system 1 is operating in the second mode, the control section 15 may inform the operator (including those which can be perceived by visual sense or auditory sense) that the second manipulator 7 and the object contact each other, and the control section 15 may prohibit the operation of the second manipulator 7 by the operation section 13. In this case, instead of the control section 15 prohibiting the operation of the second manipulator 7 by the operation section 13, the movable direction of the second manipulator 7 in the second mode may be restricted so that the second manipulator 7 can move only in the direction in which the second manipulator 7 and the object do not contact each other.

(Modification 3)

Still another modification of the above embodiment will be described.

In the present modification, as the operation in the second mode, one can be selected and set from the operations disclosed in the above embodiment, modification 1, and modification 2.

For example, the operation section 13 has a switch (not shown) for selecting an operation in the second mode.

In the medical manipulator system 1 of the present modification, since the operation in the second mode can be selected according to the operator's preference, its usability is good.

(Modification 4)

Figure 10:
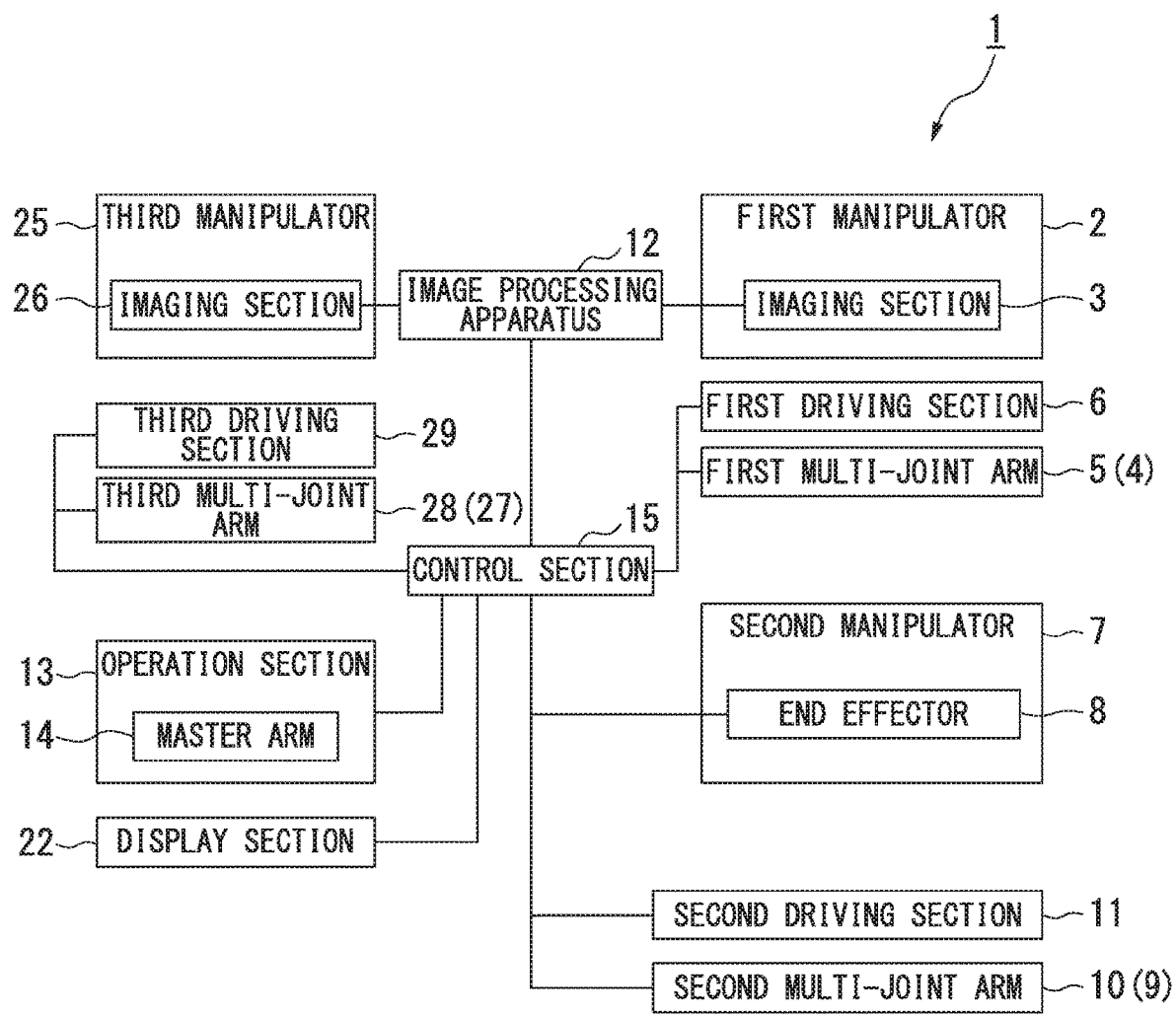
FIG. 10 is a block diagram of a medical manipulator system according to another modification of the present embodiment.

Still another modification of the above embodiment will be described. FIG. 10 is a block diagram of the medical manipulator system of the present modification.

As shown in FIG. 10, the medical manipulator system 1 of the present modification has a third manipulator 25 in addition to the first manipulator 2 and the second manipulator 7.

The third manipulator 25 is an observation device such as an endoscope for observing the inside of the body, and has an imaging section 26. Therefore, in the present modification, the third manipulator 25 can observe the treatment target portion from a viewpoint different from the imaging section 3 of the first manipulator 2.

In addition, the third manipulator 25 has a third multi-joint arm 28 (third position/orientation detection section 27) similar to the first multi-joint arm 5 and a third driving section 29 similar to the first driving section 6, and is controlled by the control section 15.

For example, similarly to the control of moving the second manipulator 7, the control section 15 of the medical manipulator system 1 of the present modification controls the third manipulator 25 according to one of the first mode, the second mode, and the third mode. The third manipulator 25 of the present embodiment is a manipulator similar to the second manipulator 7 in that it is restricted by the restriction of the operation in the second mode and the prohibition of the operation in the third mode.

In the medical manipulator system 1 of the present modification, the instrument (the second manipulator 7) that performs the treatment on the treatment target portion and the instrument (the third manipulator 25) that observes the treatment target portion from a different viewpoint from the imaging section 3 can be used in combination, and both instruments can be freely operated within a certain limitation range in the second mode, so the usability is good.

In the present modification, the manner of control in the second mode may be different corresponding to the configuration of the other manipulator used together with the first manipulator 2. For example, in the case of the second manipulator 7 having a sharp knife as the end effector 8, there is a possibility that the end effector 8 may injure the tissue unintentionally contacting the tissue in the body, so the operating speed may be reduced to such a degree that the second manipulator 7 is substantially stopped when shifting from the first mode to the second mode. Also, for example, when there is little adverse effect though the second manipulator 7 touches the tissue in the body, the control section 15 may control the operation of the second manipulator 7 so that a part of the operation of the second manipulator 7 is permitted in the third mode.

In the second mode, the moving direction of the second manipulator 7 may be limited so that the second manipulator 7 can move only in the direction in which the end effector 8 enters into the view field area A1 when the mode is changed from the first mode to the second mode.

(Modification 5)

Figure 11:
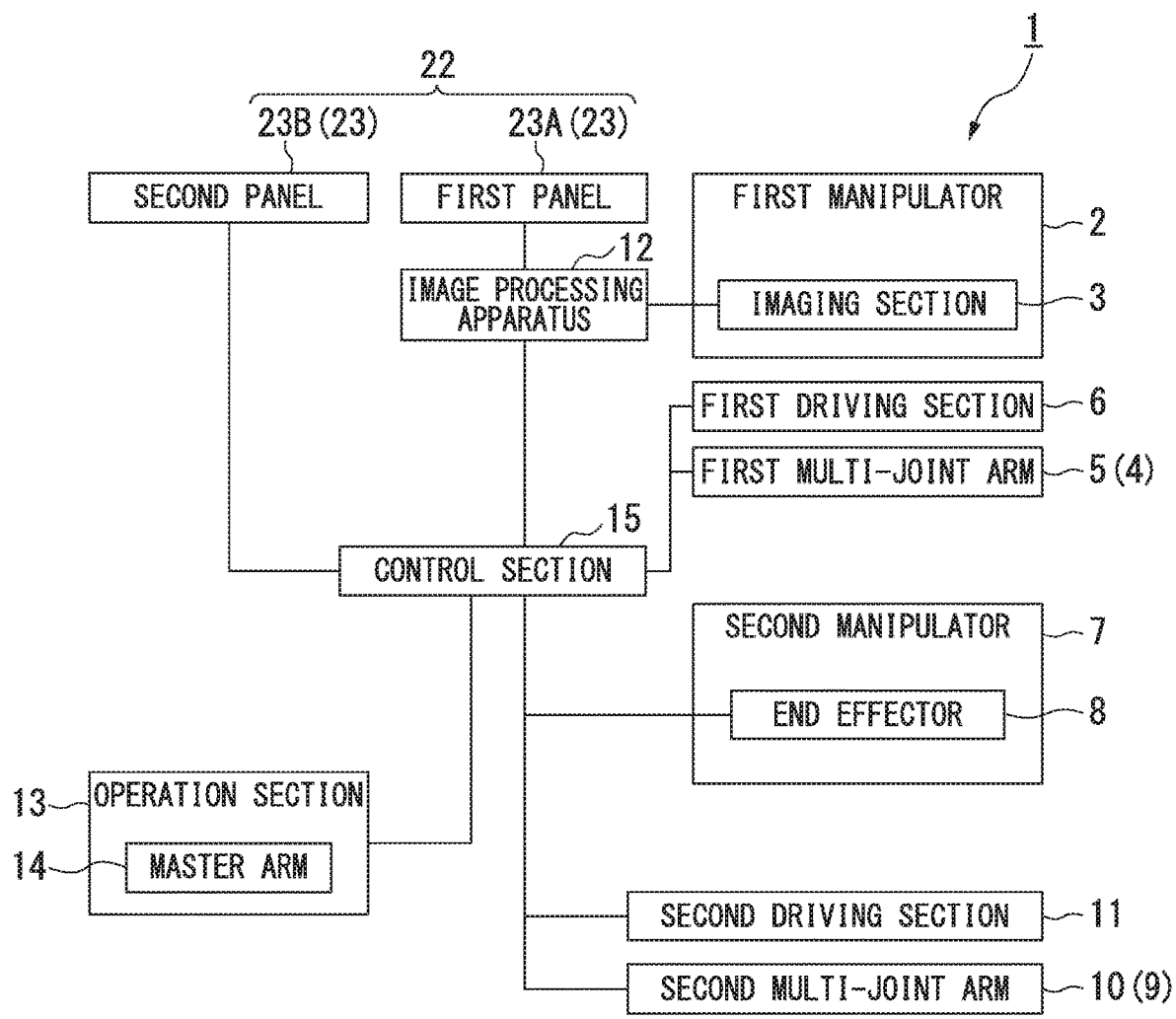
FIG. 11 is a block diagram of a medical manipulator system according to another modification of the present embodiment.

Still another modification of the above embodiment will be described. FIG. 11 is a block diagram of the medical manipulator system of the present modification. FIG. 12 is a schematic diagram showing an example of an image displayed on the display section of the medical manipulator system of the present modification.

As shown in FIG. 11, in the present modification, instead of the above-described image superimposing section 19, an image output section 30 is provided for displaying the image imaged by the imaging section 3 and the image generated by the image generating section 18 respectively on separate display panels 23. The display section 22 includes a first panel 23A serving as the view field display section 22a for displaying the image imaged by the imaging section 3 and a second panel 23B serving as the auxiliary display section 22b capable of displaying the index M corresponding to the presence of the second manipulator 7.

In the present modification, for example, the image imaged by the imaging section 3 and the image including the index M are displayed on different display panels 23 (the first panel 23A and the second panel 23B). Therefore, even if the directions of view fields of the image imaged by the imaging section 3 and the image including the index M are different from each other, there is little discomfort. For example, as shown in FIG. 12, the image generating section 18 (see FIG. 11) generates an overhead view image including the first manipulator 2 and the second manipulator 7 as computer graphics, and the first manipulator 2 and the second manipulator 7 can be shown on the second panel 23B for easy understanding. Further, the control section 15 may draw the marker line L1 serving as a guide of the position of the treatment target portion on the second panel 23B. The marker line L1 is drawn on the second panel 23B, for example, based on the result of analyzing the image imaged by the imaging section 3 and measuring the distance between the imaging section 3 and the treatment target.

Further, in the present modification, it is preferable that the first panel 23A for displaying the image imaged by the imaging section 3 is arranged on the front side and the second panel 23B for displaying the above overhead view image is arranged on the lower side. In this case, the treatment target portion being imaged by the imaging section 3 is imaged in the front and the treatment is performed, and when confirming the positional relationship of each manipulator in the area including the treatment target portion, by dropping down the line of sight, it is possible to overlook the first manipulator 2 and the second manipulator 7 in a natural orientation looking down from above.

(Modification 6)

Figure 13:
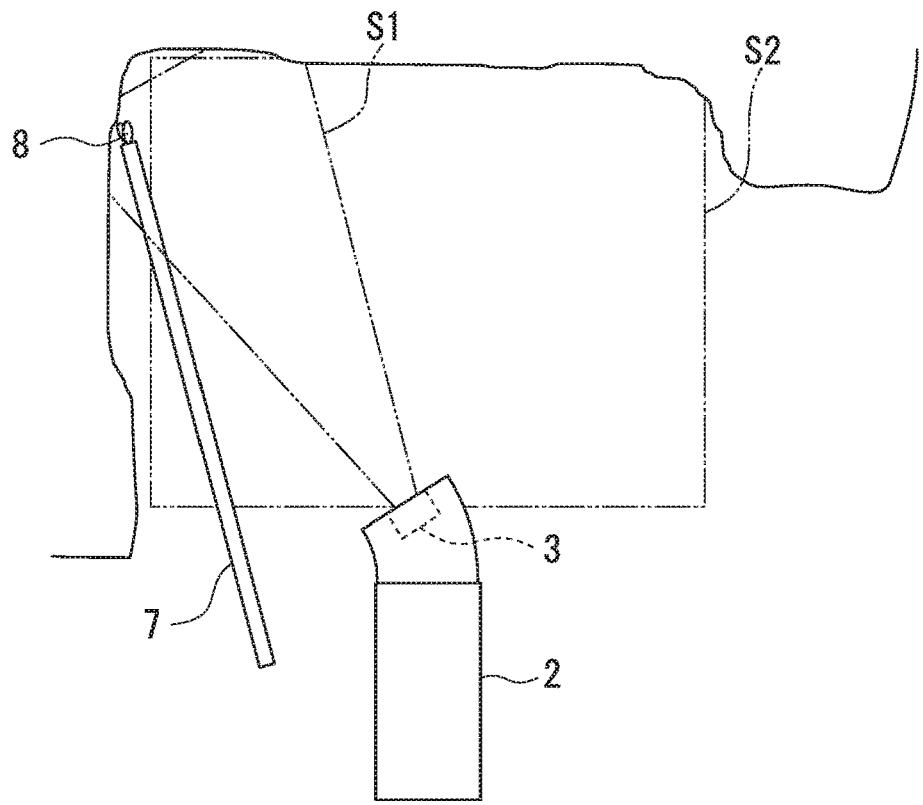
FIG. 13 is a schematic diagram showing a view field space and a boundary space defined by a medical manipulator system according to another modified example of the present embodiment.
Figure 14:
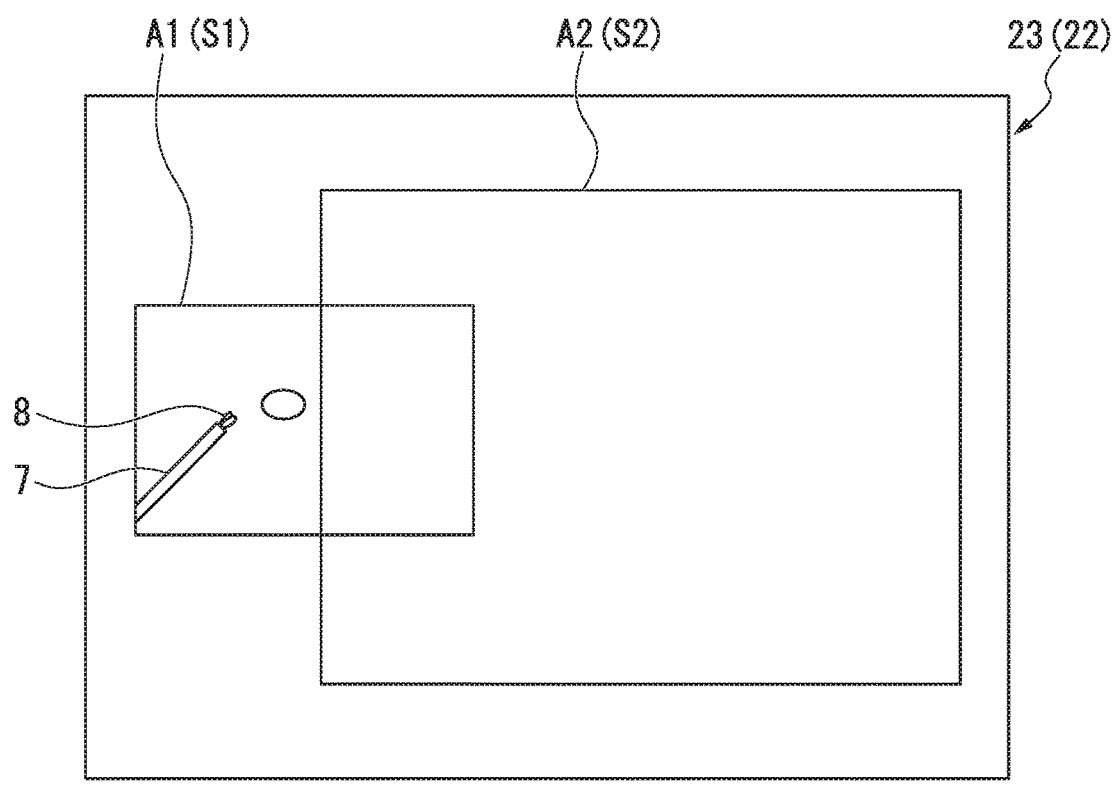
FIG. 14 is a schematic diagram showing an example of an image displayed on a display section of the medical manipulator system of the modified example.

Still another modification of the above embodiment will be described. FIG. 13 is a schematic diagram showing a view field space and a boundary space defined by the medical manipulator system of the present modification. FIG. 14 is a schematic diagram showing an example of an image displayed on the display section of the medical manipulator system of the present modification.

As shown in FIGS. 13 and 14, the present modification differs from the above embodiment at the point that a part of the view field space S1 (corresponding to the view field area A1 in the display section 23) is outside the boundary space S2 (corresponding to the boundary area A2 in the display section 23).

In the present modification, the boundary space S2 is defined as a range in which the second manipulator 7 can be operated according to the intention of the operator. In addition, in the present modification, the view field space S1 is defined based on the position and orientation of the imaging section 3 corresponding to the position of the part to be observed, independently of the movement of the second manipulator 7. Therefore, if the center of the field of view of the imaging section 3 is set in the vicinity of the outer boundary of the boundary space S2, there is a space "within the view field space S1 and outside the boundary space S2".

In the present modification, when a space in the view field space S1 and outside the boundary space S2 is included in the movable range of the second manipulator 7, the control section 15 controls the second manipulator 7 in the first mode. That is, since the space within the view field space S1 and outside the boundary space S2 can easily grasp the positional relationship between the tissue and the second manipulator 7 using the imaging section 3, the control of the second manipulator 7 is not limited.

In the present modification, in order to display both the view field area A1 corresponding to the view field space S1 and the boundary area A2 corresponding to the boundary space S2 on the display section 22, the view field area A1 and the boundary area A2 are displayed in the displayable area on the display section 22, as shown in FIG. 14. In this case, the operator can easily grasp that the second manipulator 7 is operating outside the boundary area S2, and the operator can easily judge which direction the second manipulator 7 is moved is more appropriate.

In the present modification, different control from the first mode of the above embodiment may be performed in that the second manipulator 7 informs the operator that the second manipulator 7 is operating outside the boundary area S2. For example, the control section 15 may include a fourth mode (see FIG. 15) in which the operator can freely move the master arm 14 without allowing the resistance means to function as a resistance while informing the operator that the second manipulator 7 is operating outside the boundary area S2 as the control mode. In this case, the determination section 21 selects the fourth mode when the second position P2 located is in the view field space S1 (the second position P2 is located in the view field area A1 on display of the display section 22) and the distance between the first position P1 and the second position P2 (distance measured along a plane orthogonal to the direction of view field of the imaging section 3) exceeds the predetermined value.

While preferred embodiments of the invention have been described and shown above, it should be understood that these are exemplary of the invention and are not to be considered as limiting. Additions, omissions, substitutions, and other modifications can be made without departing from the spirit or scope of the present invention.

For example, the restrictions according to the second mode in the above embodiment and each modification thereof may be appropriately combined. For example, when shifting from the first mode to the second mode, the moving speed of the second manipulator 7 may be lowered and the feedback force amount based on the tactile sensor 24 may be increased.

Further, as the second manipulator 7 approaches the outer boundary of the boundary space S2 in the second mode, the restriction content may become gradually stricter. For example, with respect to the position of the end effector 8 of the second manipulator 7, if there is the end effector 8 at a position close to the view field space S1 within the boundary space S2, only the operation speed of the second manipulator 7 may be limited, and if there is the end effector 8 at a position close to the outer boundary within the boundary space S2, the operation method of the second manipulator 7 may be limited in addition to the limitation on the operation speed of the second manipulator 7.

Design changes and the like with respect to the specific configuration are not limited to the above items.

The present invention can be applied to a manipulator system.

What is claimed is:

1. A medical manipulator system comprising:
   a first manipulator configured to change a position of an imaging sensor that images a target portion in a body;
   a second manipulator configured to change a position of an end effector that treats the target portion;
   a display configured to display images from a view field area of the imaging sensor; and
   a controller configured to:
      generate an operation command for operating the first manipulator or the second manipulator;
      select one of a plurality of control modes and control the first manipulator or the second manipulator based on the operation command,
      acquire an image of a predetermined portion imaged by the imaging sensor to acquire the view field area including a center of field of view;
      acquire a first position that is a position at a center of the view field area, and acquire a second position that is a position of a tip of the end effector within the view field area or outside the view field area as long as the second manipulator can move while imaging the predetermined portion; and
      select one mode from the plurality of control modes based on the view field area, the first position, and the second position,
   wherein the plurality of control modes include:
      a first mode in which operation of the second manipulator is fully permitted;
      a second mode in which a predetermined restriction is imposed on the operation command section and operation of the second manipulator is permitted within the restriction; and
      a third mode in which operation of the second manipulator is inhibited, and
   the controller is configured to:
      select the first mode when the second position is within the view field area,
      select the second mode when the second position is outside the view field area and a distance between the first position and the second position is equal to or less than a predetermined value, and
      select the third mode when the second position is outside the view field area and the distance between the first position and the second position is more than the predetermined value.

2. The medical manipulator system according to claim 1, wherein the display comprises:
   a view field display configured to display the image imaged by the imaging sensor; and
   an auxiliary display configured to display an index corresponding to a presence of the second manipulator.

3. The medical manipulator system according to claim 1, wherein, in the second mode, an operating speed of the second manipulator is restricted so that the second manipulator is operated with a lower speed than an operating speed of the second manipulator in the first mode.

4. The medical manipulator system according to claim 1, wherein, in the second mode, an operable direction of the second manipulator is restricted as compared with an operable direction of the second manipulator in the first mode.

5. The medical manipulator system according to claim 4, wherein, in the second mode, the operable direction is restricted to only be a direction in which the second position is directed toward the view field area.

6. The medical manipulator system according to claim 1, wherein the controller is further configured to set contents of the restriction in the second mode.

7. The medical manipulator system according to claim 1, wherein the second manipulator further includes a contact sensor configured to detect that the second manipulator has touched an object, and in the second mode, when the contact sensor detects that the second manipulator and the object are in contact with each other, an operator is notified that the second manipulator and the object have come into contact with each other and the control mode shifts to the third mode.

8. A control apparatus of a medical manipulator system, comprising a controller configured to control a first manipulator having an imaging sensor configured to image a target portion in a body and a second manipulator configured to treat the target portion in the body, based on an operation command by selecting one mode from a plurality of control modes,
   wherein the controller is configured to:
      acquire an image of a predetermined portion imaged by the imaging sensor to acquire a view field area including a center of field of view;
      acquire a first position that is a position at a center of the view field area, and acquire a second position that is a position of a tip of an end effector of the second manipulator within the view field area or outside the view field area as long as the second manipulator can move while imaging the predetermined portion; and select one mode from the plurality of control modes based on the view field area, the first position, and the second position,
wherein the plurality of control modes include:
a first mode in which operation of the second manipulator is fully permitted;
a second mode in which a predetermined restriction is imposed on the operation command and operation of the second manipulator is permitted within the restriction; and
a third mode in which operation of the second manipulator is inhibited,
the controller is configured to:
select the first mode when the second position is within the view field area,
select the second mode when the second position is outside the view field area and a distance between the first position and the second position is equal to or less than a predetermined value, and
select the third mode when the second position is outside the view field area and the distance between the first position and the second position is more than the predetermined value.

9. A method of controlling a medical manipulator system, wherein the medical manipulator system includes a first manipulator having an imaging sensor, a second manipulator having an end effector, and a display for displaying an image from a view field area of the imaging sensor, the method comprising:
acquiring an image imaged by the imaging sensor to acquire the view field area including a center of field of view;
acquiring a first position that is a position at a center of the view field area and a second position that is a position of a tip of the second manipulator;
selecting one mode from a plurality of control modes based on the view field area, the first position, and the second position, the plurality of control modes including a first mode in which operation of the second manipulator is fully permitted, a second mode in which a predetermined restriction is imposed on the operation command and operation of the second manipulator is permitted within the restriction, and a third mode in which operation of the second manipulator is inhibited; and
selecting the first mode when the second position is within the view field area, the second mode when the second position is outside the view field area and a distance between the first position and the second position is equal to or less than a predetermined value, or the third mode when the second position is outside the view field area and the distance between the first position and the second position is more than the predetermined value.

10. The method of controlling a medical manipulator system according to claim 9, further comprising:
displaying the image imaged by the imaging sensor; and
displaying an index corresponding to a presence of the second manipulator.

11. The method of controlling a medical manipulator system according to claim 9, further comprising restricting, in the second mode, an operating speed of the second manipulator so that the second manipulator is operated with a lower speed than an operating speed of the second manipulator in the first mode.

12. The method of controlling a medical manipulator system according to claim 9, further comprising restricting, in the second mode, an operable direction of the second manipulator as compared with an operable direction of the second manipulator in the first mode.

13. The method of controlling a medical manipulator system according to claim 12, further comprising restricting, in the second mode, the operable direction to only be a direction in which the second position is directed toward the view field area.

14. The method of controlling a medical manipulator system according to claim 9, further comprising setting contents of the restriction in the second mode.

15. The method of controlling a medical manipulator system according to claim 9, further comprising:
detecting that the second manipulator has touched an object; and
when the second manipulator and the object are detected to be in contact with each other in the second mode, notifying an operator that the second manipulator and the object have come into contact with each other and prohibiting operation of the second manipulator.

* * * * *